United States Patent [19]

Kleinstuck

[11] 4,045,460
[45] Aug. 30, 1977

[54] PREPARATION OF AMINOALKYLSILANES

[75] Inventor: Roland Kleinstück, Cologne, Germany

[73] Assignee: Bayer Aktiengesellschaft, Leverkusen, Germany

[21] Appl. No.: 681,020

[22] Filed: Apr. 28, 1976

[30] Foreign Application Priority Data

May 14, 1975 Germany .................. 2521399

[51] Int. Cl.$^2$ .................. C07F 7/10; C07F 7/18
[52] U.S. Cl. .................. 260/448.8 R; 260/448.2 E
[58] Field of Search .................. 260/448.8 R, 448.2 E

[56] References Cited

U.S. PATENT DOCUMENTS

| | | | |
|---|---|---|---|
| 2,930,809 | 3/1960 | Jex et al. | 260/448.8 R |
| 3,341,563 | 9/1967 | Buchheit et al. | 260/448.8 R |
| 3,481,964 | 12/1969 | Ismail et al. | 260/448.2 E |
| 3,504,007 | 3/1970 | Owen et al. | 260/448.8 R X |
| 3,927,057 | 12/1975 | Takamizawa | 260/448.2 E |

FOREIGN PATENT DOCUMENTS 1,238,875   7/1971   United Kingdom ... 260/448.8 R UX

OTHER PUBLICATIONS

"Journ. of Pharm. Sci.", 60, p. 1120 (1971).
"Iz. Akad. Nauk SSR Ser. Chim.," p. 1878, 1960.

Primary Examiner—Paul F. Shaver
Attorney, Agent, or Firm—Burgess, Dinklage & Sprung

[57] ABSTRACT

In the preparation of an aminoalkylsilane of the formula $$(RO)_{3-n}R_n'SiR^2NH_2$$

wherein
n is an integer from 0 to 3,
R is an alkyl or alkoxyalkyl radical with 1 to 8 C atoms in each alkyl radical, or an aryl radical with up to 10 C atoms,
R$^1$ is an alkyl radical with up to 8 C atoms or an aryl radical with up to 10 C atoms, and
R$^2$ is a divalent hydrocarbon radical with 2 to 10 C atoms, by reacting the corresponding halogenoalkylsilane with excess ammonia at a temperature above about 80° C, and working up the reaction mixture, the improvement which comprises adding a metal alcoholate to the reaction mixture obtained from the amination before the mixture is worked up. The alcoholate may be added in an amount equivalent to the halogenoalkylsilane initially employed or to the halide content of the filtrate after amination but before working up, as by distillation.

5 Claims, No Drawings

PREPARATION OF AMINOALKYLSILANES

The present invention relates to an improved process for the preparation of aminoalkylsilanes of the general formula $$(RO)_{3-n}R_n{}^1SiR^2NH_2$$

wherein
- n is an integer from 0 to 3,
- R is an alkyl or alkoxyalkyl radical with 1 to 8 C-atoms in each alkyl radical, or an aryl radical with up to 10 C-atoms,
- R¹ is an alkyl radical with up to 8 C atoms or an aryl radical with up to 10 C atoms and
- R² is a divalent, optionally unsaturated hydrocarbon radical with 2 to 10 C atoms.

Aminoalkylsilanes are in themselves known and are used in a variety of ways as adhesion promoters for inorganic materials, for example glass fibers, with organic polymers. They are also used to protect inorganic oxides or metallic surfaces. The preparation of aminoalkylsilanes according to known processes has, however, a number of disadvantages. Thus, for example, the platinum-catalyzed addition reaction of allylamine with hydrogenoalkoxysilanes (German Published Specification DOS No. 1.793,280), which in itself is a technically simple process, allows only little variation and gives a mixture of isomers consisting of β- and γ-functional silylalkylamines. Furthermore, the use of hydrogenoalkoxysilanes which, in addition to being highly toxic (compare, for example, Journ. of Pharm. Sci. 60 (1971) 1120) are extremely difficult to prepare and handle, is undesirable.

A further process for the preparation of aminoalkylsilanes is the reduction of silylalkylnitriles with hydrogen under pressure in the presence of a catalyst. However, this method is restricted to the preparation of those silylalkylamines in which silicon and nitrogen are separated by at least 3 C atoms (U.S. Pat. No. 2,930,809 and Iz. Akad. Nauk. SSSR, Ser. Chim. 1960, 1878).

A further process which can be generally employed is the amination of halogenoalkylsilanes. German Published Specification DAS No. 1,023,462 describes a procedure in which γ-chloropropylalkoxysilanes are reacted with an approximately 20-fold excess of ammonia in an autoclave. However, the yield of mono-alkoxysilylpropylamine reaches only 50%.

It is therefore an object of the present invention to find a process which does not exhibit the said disadvantages.

The object of the present invention is realized by a process for the preparation of aminoalkylsilanes of the formula $$(RO)_{3-n}R_n{}^1SiR^2NH_2$$

wherein
- n is an integer from 0 to 3,
- R is an alkyl or alkoxyalkyl radical with 1 to 8 C-atoms in each alkyl radical, or an aryl radical with up to 10 C-atoms,
- R¹ is an alkyl radical with up to 8 C atoms or an aryl radical with up to 10 C atoms and
- R² is a divalent, optionally unsaturated hydrocarbon radical with 2 to 10 C atoms, by reacting the corresponding halogenoalkylsilanes with excess ammonia, if appropriate in the presence of a solvent, at temperatures above 80° C, which process is characterized in that a metal alcoholate is added to the reaction mixture obtained from the amination before this mixture is worked up.

The process according to the invention may be carried out in such a way that the reaction mixture obtained from the amination (such as is described, for example, in German Published Specification DAS No. 1,023,462 is treated with an amount of a metal alcoholate which is approximately equivalent to the amount of halogenoalkylsilane employed. The mixture is then stirred briefly until any evolution of gas which may occur has ceased and is then filtered in the customary manner and the silane is separated off, for example by distillation. If appropriate, a solvent, such as, for example, toluene, hexane or an alcohol, the recommended alcohol being that which forms the alkoxy group, can also be added to the reaction mixture before, or also only after, the amination.

In a preferred alternate embodiment of the process according to the invention the mixture obtained from the amination in excess ammonia, if appropriate in the presence of solvent, is filtered after releasing the pressure, if necessary after diluting with solvent. The halide content of the filtrate is determined and the equivalent amount of alcoholate is added, while stirring. Stirring is continued for a short time, the mixture is filtered and any solvent which may have been added, and the alcohol liberated from the alcoholate, are stripped from the filtrate, which is fractionated.

Suitable starting materials for the process according to the invention are the halogenoalkyl(alkoxy)silanes which correspond to the abovementioned formula. Preferred radicals for R are alkyl or alkoxyalkyl radicals wherein each alkyl moiety has up to 4, and especially up to 3, carbon atoms, or aryl radicals with up to 7 carbon atoms, especially phenyl radicals; preferred radicals for R¹ are alkyle radicals with up to 5 C-atoms, and especially up to 2, carbon atoms, or phenyl radicals; preferred radicals for R² are divalent hydrocarbon radicals with 2 to 6, especially 2 to 4 C-atoms. Substances such as $(CH_3O)_3Si-(CH_2)_3-Cl$, $(C_2H_5O)_3Si-(CH_2)_3-Cl$, $(C_2H_5O)_3Si-(CH_2)_3-Br$, $(CH_3O)_2(CH_3)Si-(CH_2)_3-Cl$, $(CH_3O)(CH_3)_2Si-(CH_2)_3-Cl$, $(C_2H_5O)_2(CH_3)Si-(CH_2)_3-Cl$, $(C_2H_5O)(CH_3)_2Si-(CH_2)_3-Cl$, $(CH_3O)_2(C_6H_5)Si-(CH_2)_3-Cl$, $(C_3H_7O)_3Si-(CH_2)_3-Cl$, $(C_2H_5O)_3Si-(CH_2)_2-Cl$, $(CH_3O)_3Si-(CH_2)_4-Cl$, $(C_6H_5O)_3Si-(CH_2)_3-Cl$ and $(CH_3-O-C_2H_4O)_3Si-(CH_2)_3-Cl$ are preferentially employed.

The alcoholate employed can be the metal salt of any desired alcohol, such as, for example, an alkali metal, alkaline earth metal or aluminum alcoholate of a lower alkanol containing up to 4 carbon atoms, e. g. Na methylate, Na ethylate, Na propylate, Na isopropylate, Na butylate, K methylate, K ethylate, Mg methylate, Mg ethylate, Ca methylate, Ca ethylate, Al ethylate.

However, because of the danger of trans-esterification at the silicon, it is advisable, when preparing alkoxysilylalkylamines, to use the alcohol which forms the alkoxy group, or a lower-boiling alcohol, the methylate, especially sodium methylate, being preferred because of its high stability even as a solid. The alcoholate is added as a solid, in suspension or in a solvent, preferably in the corresponding alcohol.

The process according to the invention will now be explained in more detail with the aid of the examples which follow:

EXAMPLE 1

The crude product obtained from the methoxylation of 1 mole of γ-chloropropyl-trichlorosilane (which contains 0.97 mole of γ-chloropropyl-trimethoxysilane), 1 g of potassium iodide, 200 ml of dry methanol and 450 g of dry ammonia are allowed to react for 6 hours at 110° C in a 2.5 l tumbling autoclave. After cooling and releasing the pressure, the mixture is diluted with 1 l of dry methanol and filtered. A chloride titration shows that the solution contains 0.90 mole of Cl⁻. Accordingly, 0.90 mole of sodium methylate, dissolved in 210 ml of methanol, are added, while stirring. After stirring for 30 minutes, the mixture is filtered. The methanol is stripped off under reduced pressure and the residue is fractionated. 125 g of γ-aminopropyl-trimethoxysilane distill at 0.4 mm Hg and at 55° to 58° C; neutralization equivalent: found: 181, calculated: 179; refractive index: $n_b^{20}$: 1.4240. A further 6 g of γ-aminopropyl-trimethoxysilane are obtained, in addition to bis-trimethoxy-silylpropylamine, in the last runnings so that the yield, relative to γ-chloropropyl-trichlorosilane employed, is 73%.

COMPARATIVE EXAMPLE

A batch which was run analogously to Example 1 but without adding the methylate gave 53 g (30%) of γ-aminopropyl-trimethoxysilane

EXAMPLE 2

The crude product obtained from the methoxylation of 1 mole of γ-chloropropyl-trichlorosilane (which contains 0.97 mole of γ-chloropropyl-trimethoxysilane), 1 g of potassium iodide, 200 ml of dry methanol and 450 g of dry ammonia are allowed to react for 6 hours at 110° C in a 2.5 l tumbling autoclave. After cooling and releasing the pressure, the mixture is diluted with 1 l of dry methanol and 54 g (1 mol) of sodium methylate are added in increments, while stirring, to the suspension thus obtained. After stirring for 30 minutes, the mixture is filtered and the filtrate is distilled. 119 g of γ-aminopropyl-trimethoxysilane distill at 2 mm Hg and at 60° to 63° C; neutralization equivalent: found: 180; calculated: 179; refractive index: $n_b^{20}$:1.4238. The last runnings contain, in addition to bis-(trimethoxysilylpropyl)-amine, a further 14 g of γ-aminopropyl-trimethoxysilane, so that the total yield, relative to γ-chloropropyl-trichlorosilane employed, is 133 g (74%).

EXAMPLE 3

The crude product obtained from the ethoxylation of 1 mole of γ-chloropropyl-trichlorosilane (which contains about 0.98 mole of γ-chloropropyl-triethoxysilane), 1 g of potassium iodide, 200 ml of dry ethanol and 450 g of dry ammonia are allowed to react for 6 hours at 110° C in a 2.5 l tumbling autoclave. After cooling and releasing the pressure, the mixture is diluted with 1 l of dry ethanol and filtered. A titration shows that the solution contains 0.36 mole of Cl⁻. Accordingly, 0.36 mole of sodium ethylate, in 130 ml of ethanol, are added to the solution, while stirring, and the mixture is stirred for a further 30 minutes and filtered. The ethanol is stripped off under reduced pressure and the residue is fractionated. At 0.4 mm Hg and a top temperature of 75°-80° C, 154 g of γ-aminopropyl-triethoxysilane are obtained; neutralization equivalent: found: 223; calculated: 221; refractive index $n_o^{20}$: 1.4218. This corresponds to a yield of 70%, relative to γ-chloropropyl-trichlorosilane employed.

EXAMPLE 4

227 g (1 mole) of β-chloroethyltriethoxysilane and 400 g of dry ammonia are allowed to react for 6 hours at 100° C in a 2.5 l tumbling autoclave. After cooling and releasing the pressure, the mixture is diluted with 1 l of dry ethanol and filtered. A chloride titration shows that the solution contains 0.43 mole of Cl⁻. Accordingly, 0.43 mole of sodium ethylate, dissolved in 170 ml of ethanol, are added, while stirring. After stirring for 30 minutes, the mixture is filtered. The ethanol is stripped off under reduced pressure and the residue is fractionated. 130 g (63%) of γ-aminoethyl-triethoxysilane distil at 12 mm Hg and 92° to 94° C. Neutralization equivalent: found: 206; calculated: 207; refractive index $n_b^{20}$: 1.4172.

EXAMPLE 5

The crude product obtained from the ethoxylation of 1 mole of γ-chloropropyl-methyldichlorosilane (which contains 0.96 mole of γ-chloropropyl-methyldiethoxysilane), 1 g of potassium iodide and 410 g of dry ammonia are allowed to react for 6 hours at 110° C in a 2.5 l tumbling autoclave. After cooling and releasing the pressure, the mixture is diluted with 0.5 l of dry ethanol and filtered. A chloride titration shows that the solution contains 0.29 mole of Cl⁻. 0.29 mole of sodium methylate, in 100 ml of ethanol, are added, while stirring, and the mixture is stirred for a further 30 minutes and filtered. The alcohol mixture is distilled off and the residue is fractionated under reduced pressure. At 4 mm Hg and a head temperature of 73°-75° C, 140 g of γ-aminopropyl-methyldiethoxysilane are obtained. Neutralization equivalent: found: 193; calculated: 191; refractive index $n_D^{20}$: 1.4262. This corresponds to a yield of 73%, relative to γ-chloropropyl-methyldichlorosilane employed.

It will be appreciated that the instant specification and examples are set forth by way of illustration and not limitation, and that various modifications and changes may be made without departing from the spirit and scope of the present invention.

What is claimed is:

1. In the preparation of an aminoalkylsilane of the formula $$(RO)_{3-n}R_n^1SiR^2NH_2$$

wherein n is an integer from 0 to 3,

R is an alkyl or alkoxyalkyl radical with 1 to 8 C atoms in each alkyl radical, or an aryl radical with up to 10 C atoms, R¹ is an alkyl radical with up to 8 C atoms or an aryl radical with up to 10 C atoms, and R² is a divalent hydrocarbon radical with 2 to 10 C atoms, by reacting the corresponding halogenoalkylsilane with excess ammonia at a temperature above about 80° C, and working up the reaction mixture, the improvement which comprises adding a metal alcoholate to the reaction mixture obtained from the amination before the mixture is worked up.

2. The process according to claim 1, wherein the alcoholate is added in an amount approximately equivalent to the amount of Cl³¹ contained in the reaction mixture formed during the amination after the reaction mixture has been filtered.

3. The process according to claim 1, wherein working up of the reaction mixture is effected by distillation and the alcoholate is added to the reaction mixture before distillation in an amount approximately equivalent to the chloroalkylsilane initially employed.

4. The process according to claim 1, wherein the alcoholate is sodium methylate.

5. The process according to claim 2, wherein the halogenoalkyl silane is selected from the group consisting of $(CH_3O)_3Si-(CH_2)_3-Cl$, $(C_2H_5O)_3Si-(CH_2)_3-Cl$, $(C_2H_5O)_3Si-(CH_2)_3-Br$, $(CH_3O)_2(CH_3)Si-(CH_2)_3-Cl$, $(CH_3O)(CH_3)_2Si-(CH_2)_3-Cl$, $(C_2H_5O)_2(CH_3)Si-(CH_2)_3-Cl$, $(C_2H_5O)(CH_3)_2Si-(CH_2)_3-Cl$, $(CH_3O)_2(C_6H_5)Si-(CH_2)_3-Cl$, $(C_3H_7O)_3Si-(CH_2)_3-Cl$, $(C_2H_5O)_3Si-(CH_2)_2-Cl$, $(CH_3O)_3Si-(CH_2)_4-Cl$, $(C_6H_5C)_3Si-(CH_2)_3-Cl$ and $(CH_3-O-C_2H_4O)_3Si-(CH_2)_3-Cl$, and the alcoholate is selected from the group consisting of Na methylate, Na ethylate, Na isopropylate, Na tertiary butylate, Na tertiary amylate, K methylate, K ethylate, K tertiary butyl, Mg methylate, Mg ethylate, Ca methylate, Ca ethylate and Al ethylate.

* * * * *